(12) United States Patent  (10) Patent No.: US 10,148,162 B2
Choi et al.  (45) Date of Patent: Dec. 4, 2018

(54) SYSTEM FOR CONTROLLING MICRO-ROBOT USING TRANSFER ROBOT

(71) Applicant: Daegu Gyeongbuk Institute of Science and Technology, Daegu (KR)

(72) Inventors: Hong Soo Choi, Daegu (KR); Seong Yong Woo, Daegu (KR); Sang Won Kim, Daegu (KR)

(73) Assignee: Daegu Gyeongbuk Institute of Science and Technology, Daegu (KR)

( * ) Notice: Subject to any disclaimer, the term of this patent is extended or adjusted under 35 U.S.C. 154(b) by 26 days.

(21) Appl. No.: 15/044,543

(22) Filed: Feb. 16, 2016

(65) Prior Publication Data

US 2016/0241121 A1  Aug. 18, 2016

(30) Foreign Application Priority Data

Feb. 17, 2015  (KR) .......................... 10-2015-0023998

(51) Int. Cl.
*H02P 9/14* (2006.01)
*H02K 41/035* (2006.01)
(Continued)

(52) U.S. Cl.
CPC ......... *H02K 41/0352* (2013.01); *A61B 34/30* (2016.02); *A61B 34/35* (2016.02); *A61B 34/72* (2016.02); *A61B 34/73* (2016.02); *G05B 1/01* (2013.01); *G05B 19/19* (2013.01); *H02K 41/031* (2013.01); *H02K 41/035* (2013.01); *G05B 2219/41355* (2013.01); *G05B 2219/45073* (2013.01); *H02K 21/021* (2013.01)

(58) Field of Classification Search
CPC .. H02J 50/90; H02J 7/328; H02P 9/14; H02K 44/20; H02K 44/26; B25J 19/00
See application file for complete search history.

(56) References Cited

U.S. PATENT DOCUMENTS 5,610,488 A *  3/1997  Miyazawa ................. B25J 5/00
  318/16
8,515,578 B2 *  8/2013  Chiappetta ........... G05D 1/0272
  180/167

(Continued)

FOREIGN PATENT DOCUMENTS

KR  10-2009-0109818 A  10/2009
KR  10-1001291 B1  12/2010
(Continued)

OTHER PUBLICATIONS

Korean Intellectual Property Office; Communication dated Aug. 30, 2017 in counterpart Korean application No. 10-2015-0023998.

*Primary Examiner* — Bickey Dhakal
(74) *Attorney, Agent, or Firm* — Sughrue Mion, PLLC

(57) ABSTRACT

Disclosed is a system for performing a control on a micro-robot using a transfer robot. The system includes a magnetic field control unit configured to control a movement of a micro-structure or a micro-robot within a working area according to an output magnetic field, a transfer robot connected to the magnetic field control unit to transfer the working area in space, and a control unit configured to receive position information about the micro-structure or micro-robot and position information about the transfer robot, and transmit a control signal based on the received position information.

8 Claims, 2 Drawing Sheets

(51) Int. Cl.
  *G05B 1/01* (2006.01)
  *H02K 41/03* (2006.01)
  *G05B 19/19* (2006.01)
  *A61B 34/30* (2016.01)
  *A61B 34/35* (2016.01)
  *A61B 34/00* (2016.01)
  *H02K 21/02* (2006.01)

(56) References Cited

U.S. PATENT DOCUMENTS

| | | |
|---|---|---|
| 9,136,051 B2 | 9/2015 | Park et al. |
| 9,373,443 B2 | 6/2016 | Kim et al. |
| 2013/0072789 A1* | 3/2013 | Park .................. H01F 7/02 600/424 |
| 2014/0253114 A1* | 9/2014 | Khamesee .......... G01R 33/07 324/251 |
| 2014/0333143 A1 | 11/2014 | Kim et al. |

FOREIGN PATENT DOCUMENTS

| | | |
|---|---|---|
| KR | 10-1084720 B1 | 11/2011 |
| KR | 10-2013-0024236 A | 3/2013 |
| KR | 10-1330533 B1 | 11/2013 |
| KR | 10-1380996 B1 | 4/2014 |
| KR | 10-1450091 B1 | 10/2014 |
| WO | 2013/032113 A1 | 3/2013 |

\* cited by examiner (a)                      (b)

SYSTEM FOR CONTROLLING MICRO-ROBOT USING TRANSFER ROBOT

CROSS-REFERENCE TO RELATED APPLICATION

This application claims priority to and the benefit of Korean Patent Application No. 10-2015-0023998, filed on Feb. 17, 2015, the disclosure of which is incorporated herein by reference in its entirety.

BACKGROUND

1. Field of the Invention

The present disclosure relates to a technology for controlling a micro-robot using a transfer robot.

2. Discussion of Related Art

A micro-robot represents a robot that has a micro size, and has been applied to medical industries, aerospace industries, national defense industries, and so on according to the form and use thereof through various methods.

A micro-robot in the form of an endoscope is used for imaging the inside of a small intestine and a large intestine, and has a size ranging from several micrometers to several millimeters.

In addition, the micro-robot for medical industries is used in a surgery and a diagnosis process as the micro-robot requires a minimum invasion when inserted into a body and ensure a local-regional access without restriction.

Methods of driving a micro-structure and a micro-robot are achieved by vibration, light, heat and electrostatic, or by directly transferring electrical energy.

A conventional micro-robot driving method using a magnetic field is achieved using various coil systems, in which each coil controls input electrical energy to drive a micro-structure or a micro-robot according to a correlation between magnetic fields of the coils.

In general, the micro-robot driving method using a magnetic field has a working area in the form of a hexahedron, and in a currently used system, the working area is set to have a width of 1 cm, a length of 1 cm, and a height of 1 cm.

In other words, the working area that corresponds to a space formed by mutual operation of a plurality of coils has a significantly small size, and in order to physically expand the working area, the size of a coil needs to be increased or a higher electrical energy needs to be supplied, which causes limitation in applying the micro-robot driving method using a magnetic field to the micro-robot.

That is, the method of increasing coil sizes has a physical limitation and the method of increasing electrical energy lowers the efficiency of a control device and a driver that are used to drive the corresponding coils, which also causes an increase in energy consumption.

SUMMARY OF THE INVENTION

The present disclosure is directed to technology for a system capable of performing a wide area control on a micro-structure or a micro-robot by expanding and changing the position of a magnetic field generation system for the micro-structure or the micro-robot using a transfer robot.

The technical objectives of the inventive concept are not limited to the above disclosure; other objectives may become apparent to those of ordinary skill in the art based on the following descriptions.

In accordance with one aspect of the present disclosure, there is provided a system for controlling a micro-robot using a transfer robot, the system including: a magnetic field control unit configured to control a movement of a micro-structure or a micro-robot within a working area that is determined according to an output magnetic field; a transfer robot connected to the magnetic field control unit to transfer the working area in space; and a control unit configured to receive position information about the micro-structure or micro-robot and position information about the transfer robot, and transmit a control signal based on the received position information.

As is apparent from the above, the system for controlling a micro-robot using a transfer robot according to the present disclosure can perform a wide area control that expands a working area of the micro-structure or the micro-robot in 3D space through a structural change by using a general infrastructure without needing a high electrical energy or a large coil.

The system for controlling a micro-robot using a transfer robot according to the present disclosure can perform control over a wide area in space by using a transfer robot interoperating with a magnetic field generation system.

The effect of the present invention is not limited to those mentioned above, other effects which are not mentioned will be able to be clearly understood to those skilled in the art from the following description.

BRIEF DESCRIPTION OF THE DRAWINGS

The above and other objects, features and advantages of the present disclosure will become more apparent to those of ordinary skill in the art by describing in detail exemplary embodiments thereof with reference to the accompanying drawings, in which.

DETAILED DESCRIPTION OF EXEMPLARY EMBODIMENTS

The above objects and other advantages, and a scheme for the advantages of the present invention will become readily apparent by reference to the following detailed description when considered in conjunction with the accompanying drawings.

However, the scope of the present invention is not limited to such embodiments and the present invention may be realized in various forms. The embodiments to be described below are nothing but the ones provided to bring the disclosure of the present invention to perfection and assist those skilled in the art to completely understand the present invention. The present invention is defined only by the scope of the appended claims.

The terminology used herein is for the purpose of describing particular embodiments only and is not intended to be limiting of the invention. As used herein, the singular forms "a," "an" and "the" are intended to include the plural forms as well, unless the context clearly indicates otherwise. It will be further understood that the terms "comprises," "comprising," "includes" and/or "including," when used herein, specify the presence of stated features, integers, steps, operations, elements, and/or components, but do not preclude the presence or addition of one or more other features, integers, steps, operations, elements, components, and/or groups thereof.

Figure 1:
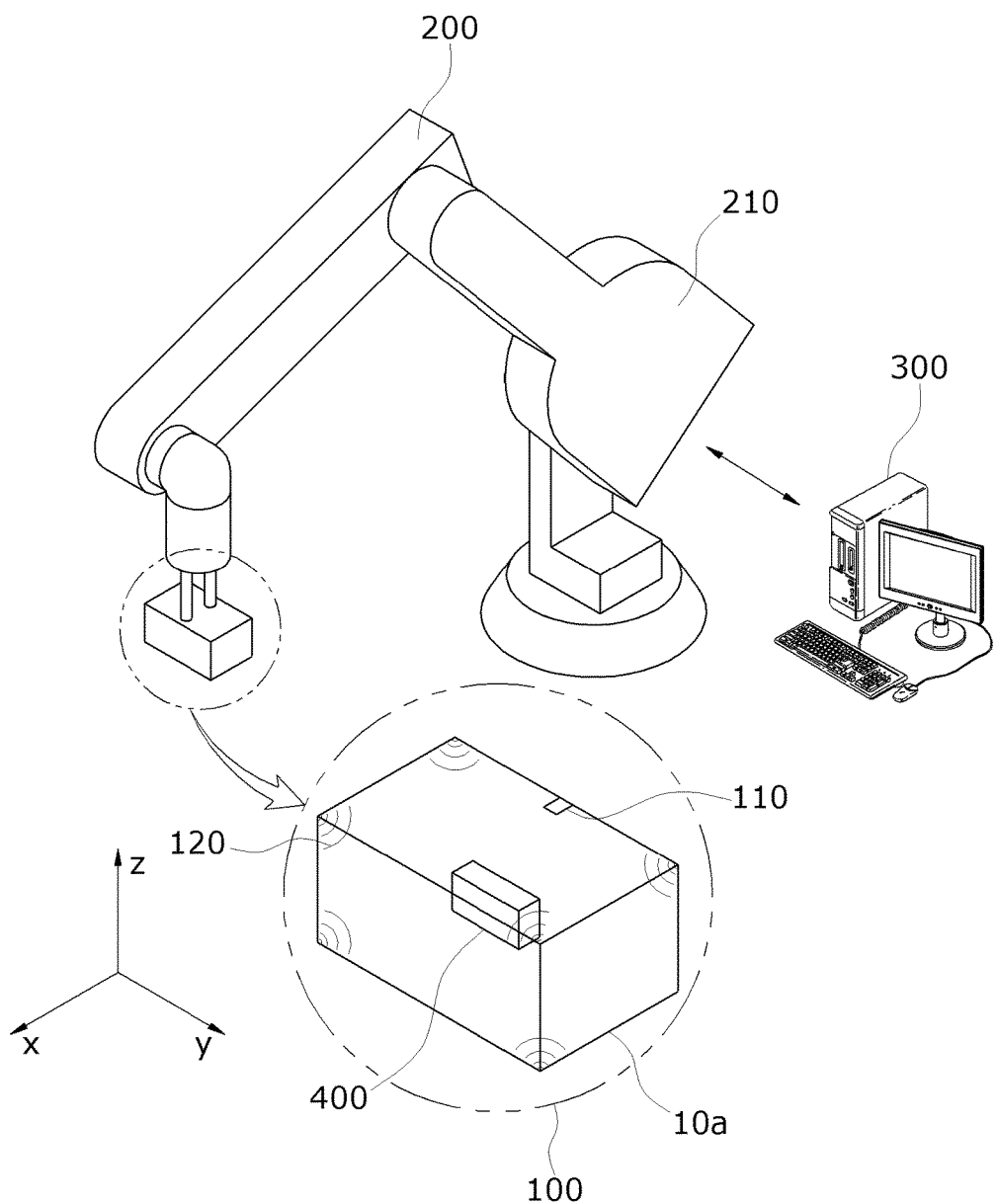
FIG. 1 is a block diagram illustrating a system for controlling a micro-robot using a transfer robot according to an exemplary embodiment of the present disclosure.

FIG. 1 is a block diagram illustrating a system for controlling a micro-robot using a transfer robot according to an exemplary embodiment of the present disclosure.

A system for controlling a micro-robot using a transfer robot according to an exemplary embodiment of the present disclosure includes a magnetic field control unit 110 configured to control a movement of a micro-structure or a micro-robot 400 within a working area 10a according to an output magnetic field, a transfer robot 200 configured to transfer the working area in space, and a control unit 300 configured to receive position information about the micro-structure or micro-robot 400 and position information about the transfer robot 200, and transmit a control signal based on the received position information.

A driving unit 100 according to an exemplary embodiment of the present disclosure is a component to drive a micro-structure or a micro-robot 400 by using a magnetic field within a working area 10a that is expanded by the transfer robot 200, and the driving unit 100 includes a magnetic field output unit 120 provided with a core, a bobbin, and a coil to output a magnetic field and the magnetic field control unit 110 that controls a movement of a micro-structure or a micro-robot 400 while interoperating with the magnetic field output unit 120.

The magnetic field control unit 110 according to an exemplary embodiment of the present disclosure communicates with the control unit 300 to perform a feedback operation using position information about a micro-structure or a micro-robot 400, and controls the micro-structure or the micro-robot 400 to be driven at a precise position in a working area 10a that is expanded.

The transfer robot 200 according to an exemplary embodiment of the present disclosure is connected to one end of the driving unit 100 including the magnetic field control unit 110 and the magnetic field output unit 120 to transfer the driving unit 100 in three-dimensional space.

In other words, according to an exemplary embodiment of the present disclosure, the transfer robot 200 is provided as a transfer device capable of controlling a micro-structure or a micro-robot 400 in a wide range of areas by changing the position of the driving unit 100 corresponding to a magnetic field generation system so as to expand a unique working area of the driving unit 100 without needing to have a large coil or a high electrical energy.

In this case, the transfer robot 200 may include at least one of a linear motion robot, a linear motion robot having a rotation axis, and a multi-joint robot.

A cartesian coordinate robot capable of linear motion is manufactured by installing a ball screw at a rotary motor or by using a linear motor.

When composed by a three axes stage, the cartesian coordinate robot may be manufactured as a robot that moves along coordinates in 3D space in X, Y, Z axes direction, ensuring high precision transfer and control.

In addition, the cartesian coordinate robot, on which an axis is additionally installed for rotational motion to perform control of four axes X, Y, Z, Θ, may serve as the transfer robot 200 according to an exemplary embodiment of the present disclosure.

A multi-joint robot is a robot which is applied to various fields, for example, industrial fields or medical fields, and freely moves along coordinates in space within a working range by joints mounted on the multi-joint robot.

According to an exemplary embodiment of the present disclosure, the driving unit 100 is mounted at one end of the above-described linear motion robot, the linear motion robot having a rotation axis, and the multi-joint robot so that a working area 10a of the driving unit 100 for a micro-structure or a micro-robot 400 may be expanded in 3D space (X, Y, Z), thereby enabling a wide area control of the micro-structure or micro-robot 400.

The control unit 300 according to an exemplary embodiment of the present disclosure monitors whether a position of a micro-structure or a micro-robot 400 lies within a preset area in a working area 10a as a result of an operation of the transfer robot 200 transferring the driving unit 100, and sends a transfer robot control unit 210 a control signal regarding a movement of the transfer robot 200 according to a result of the monitoring.

According to an exemplary embodiment of the present disclosure, the control unit 300 calculates mutual position information by using position information about a micro-structure or a micro-robot 400 and position information about the transfer robot 200 that are received by using control instructions of the transfer robot control unit 210 and the magnetic field control unit 110, an encoder of each component, and image data.

In this case, in order to acquire position information about the micro-structure or the micro-robot 400, the system according to an exemplary embodiment of the present disclosure may further include an image acquisition unit to capture a working area 10a of the driving unit 100 that is expanded.

Figure 2:
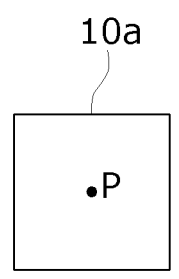
FIG. 2 is a conceptual diagram illustrating the scalability of a working area for a micro-robot using a magnetic field by a transfer robot according to an exemplary embodiment of the present disclosure.
Figure 2:
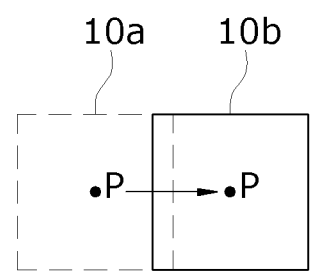

FIG. 2 is a conceptual diagram illustrating the scalability of a working area for a micro-robot using a magnetic field by a transfer robot according to an exemplary embodiment of the present disclosure.

In (a) of FIG. 2, a working area 10a before driving of the transfer robot 200 connected to the driving unit 100 is illustrated, and in (b) of FIG. 2, a working area 10b after driving of the transfer robot 200 connected to the driving unit 100 is illustrated.

In other words, the driving unit 100 is mounted at an end portion of the transfer robot 200, thereby physically expanding a working area of the driving unit 100 in 3D space that is defined by the magnetic field control unit 110 and the magnetic field output unit 120.

For example, under a preset condition that the center of a micro-structure or a micro-robot needs to be positioned at a preset point P in a working area, the control unit 300 according to an exemplary embodiment of the present disclosure receives position information about the transfer robot 200 and position information about a micro-structure or a micro-robot within a working area according to driving of the transfer robot 200 as feedback information, calculates a mutual position from the feedback information, transmits the calculated relative position to the transfer robot control unit 210 and the magnetic field control unit 110, and controls the center of the micro-structure or micro-robot to be disposed at the preset point P.

In this case, when calculating the mutual position, the control unit 300 receives respective pieces of position information by using control instructions of the transfer robot control unit 210 and the magnetic field control unit 110, an encoder of each component, and image data as described above.

Take an example in which the present disclosure is applied to a medical robot. When a patient has lesions in his or her arms and legs, the control unit 300 sends the transfer robot control unit 210 a position control signal for the transfer robot 200 according to target space coordinates 'a' being input, to drive the transfer robot 200.

Then, the control unit 300 allows the driving unit 100 disposed at the end of the transfer robot 200 to be positioned at the lesion of the arm of the patient according to the target space coordinates 'a', and sends the magnetic field control unit 110 a driving ready signal, to perform a drug delivery on the lesion of the arm.

Then, the control unit 300 allows the driving unit 100 disposed at the end of the transfer robot 200 to be positioned at the lesion of the leg of the patient by sending the transfer robot control unit 210 a position control signal for the transfer robot 200 according to target space coordinates 'b' being input to drive the the transfer robot 200, and then sends the magnetic field control unit 110 a driving ready signal, to perform a drug delivery on the lesion of the leg.

Accordingly, the control unit 300 may perform a precise control on a micro-robot or a micro-structure to be positioned at a preset point within a working area of the driving unit 100, and also perform a control to physically expand the working area of the driving unit 100 in 3D space by using the transfer robot 200.

It will be apparent to those skilled in the art that various modifications can be made to the above-described exemplary embodiments of the present disclosure without departing from the spirit or scope of the invention. Thus, it is intended that the present disclosure covers all such modifications provided they come within the scope of the appended claims and their equivalents.

What is claimed is:

1. A system comprising:
    a driving unit comprising:
        a magnetic field output unit configured to output a magnetic field; and
        a magnetic field control unit configured to control, in association with the magnetic field output unit, a movement of a micro-structure or a micro-robot within a working area of the driving unit according to an output magnetic field;
    a transfer robot connected to one end of the driving unit that includes the magnetic field output unit and the magnetic field control unit, and configured to transfer the working area of the driving unit in a three-dimensional (3D) space by moving together with the driving unit in response to an input of target space coordinates of the transfer robot, the transfer robot being different from the micro-structure or the micro-robot and configured to control the micro-structure or the micro-robot by changing a position of the driving unit; and
    a control unit configured to receive position information about the micro-structure or the micro-robot and position information about the transfer robot, and transmit a control signal based on the received position information,
    wherein the control unit, in response to the input of the target space coordinates, transmits, to a transfer robot control unit, a position control signal for the transfer robot to move the transfer robot to the target space coordinates.

2. The system of claim 1, wherein the magnetic field control unit controls the movement of the micro-structure or the micro-robot while interoperating with the magnetic field output unit that is provided with a core, a bobbin, and a coil.

3. The system of claim 1, wherein the transfer robot includes at least one of a linear motion robot, a linear motion robot having a rotation axis, and a multi-joint robot.

4. The system of claim 1, wherein the control unit monitors whether a position of the micro-structure or the micro-robot lies within a preset area in the working area as a result of an operation of the transfer robot, and transmits, to the transfer robot control unit and the magnetic field control unit, a control signal regarding the movement of the transfer robot according to a result of the monitoring.

5. The system of claim 4, further comprising an image acquisition unit configured to acquire the position information about the micro-structure or the micro-robot, wherein the control unit receives the position information about the micro-structure or the micro-robot from the image acquisition unit.

6. The system of claim 1, wherein the control unit, in response to determining, as a result of receiving the position information after driving of the transfer robot, that the transfer robot arrives at the target space coordinates, transmits a signal informing that a driving preparation is complete to the magnetic field control unit.

7. The system of claim 6, wherein the magnetic field control unit controls the movement of the micro-structure or the micro-robot while interoperating with the magnetic field output unit in response to receiving the signal informing that the driving preparation is complete.

8. A system comprising:
    a driving unit comprising:
        a magnetic field output unit configured to output a magnetic field; and
        a magnetic field control unit configured to control, in association with the magnetic field output unit, a movement of a micro-structure or a micro-robot within a working area of the driving unit according to an output magnetic field;
    a transfer robot connected to one end of the driving unit that includes the magnetic field output unit and the magnetic field control unit, and configured to transfer the working area of the driving unit in a three-dimensional (3D) space by moving together with the driving unit, the transfer robot being different from the micro-structure or the micro-robot and configured to control the micro-structure or the micro-robot by changing a position of the driving unit; and
    a control unit configured to receive position information about the micro-structure or the micro-robot and position information about the transfer robot, and transmit a control signal based on the received position information,
    wherein the control unit, in response to target space coordinates being input, transmits, to a transfer robot control unit configured to control a movement of the transfer robot, a position control signal to move the transfer robot to the target space coordinates, and
    wherein the control unit, in response to determining, as a result of receiving the position information after driving of the transfer robot, that the transfer robot arrives at the target space coordinates, transmits a signal informing that a driving preparation is complete to the magnetic field control unit.

* * * * *